(12) United States Patent
Chitre et al.

(10) Patent No.: US 7,280,875 B1
(45) Date of Patent: Oct. 9, 2007

(54) HIGH STRENGTH, LOW RESISTIVITY ELECTRODE

(75) Inventors: Yougandh Chitre, Valencia, CA (US); John R. Helland, Saugus, CA (US); Steven R. Conger, Aqua Dulce, CA (US)

(73) Assignee: Pacesetter, Inc., Sylmar, CA (US)

( * ) Notice: Subject to any disclaimer, the term of this patent is extended or adjusted under 35 U.S.C. 154(b) by 515 days.

(21) Appl. No.: 10/773,136

(22) Filed: Feb. 4, 2004

(51) Int. Cl.
*A61N 1/05* (2006.01)

(52) U.S. Cl. ............... 607/122; 174/126.1; 29/825

(58) Field of Classification Search ............... 607/115, 607/116, 122, 123; 174/96, 98, 126.1, 126.2; 29/825
See application file for complete search history.

(56) References Cited

U.S. PATENT DOCUMENTS

| | | | | |
|---|---|---|---|---|
| 4,078,299 A * | 3/1978 | Furuto et al. | ................. | 29/599 |
| 4,273,137 A * | 6/1981 | Pravoverov et al. | ........ | 607/116 |
| 4,559,951 A * | 12/1985 | Dahl et al. | ................... | 600/374 |
| 5,170,802 A | 12/1992 | Mehra | ......................... | 128/784 |
| 5,224,491 A | 7/1993 | Mehra | ......................... | 128/784 |
| 5,324,328 A * | 6/1994 | Li et al. | ..................... | 607/129 |
| 5,330,521 A | 7/1994 | Cohen | ......................... | 607/122 |
| 5,483,022 A * | 1/1996 | Mar | ......................... | 174/128.1 |
| 5,630,840 A | 5/1997 | Mayer | ............................. | 623/1 |
| 5,760,341 A | 6/1998 | Laske et al. | ............. | 174/126.2 |
| 6,720,497 B1 * | 4/2004 | Barsne | ................... | 174/102 R |
| 7,065,411 B2 * | 6/2006 | Verness | ...................... | 607/116 |
| 2003/0032997 A1 | 2/2003 | Pianca et al. | ............... | 607/117 |

* cited by examiner

*Primary Examiner*—Kennedy J. Schaetzle

(57) ABSTRACT

For use in an implantable medical device, there is provided a biocompatible, biostable, corrosion-resistant wire strand comprising a core comprising a plurality of electrically conductive, low electrical resistance filaments embedded in an electrically conductive matrix, and a low electrical resistance, substantially chemically inactive cladding.

4 Claims, 3 Drawing Sheets

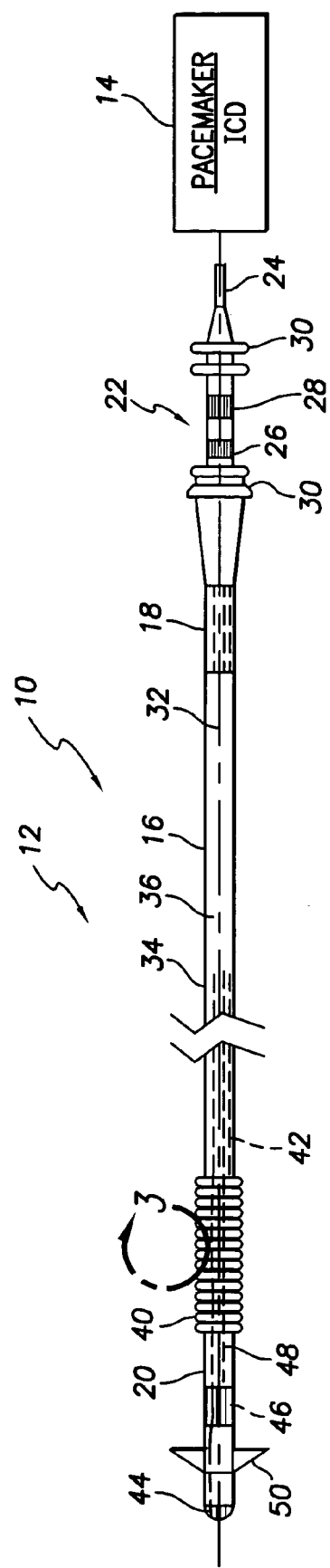

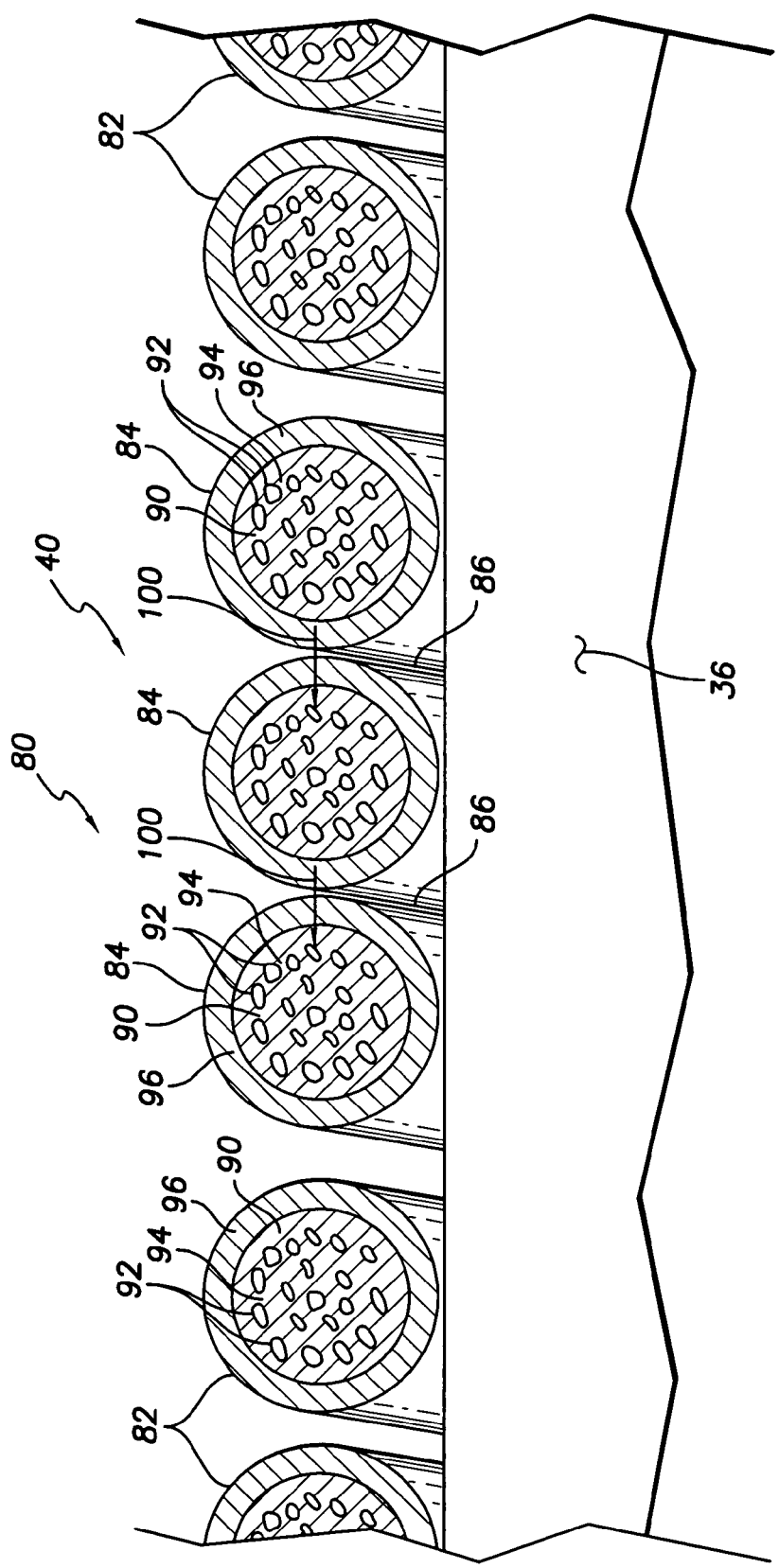

HIGH STRENGTH, LOW RESISTIVITY ELECTRODE

FIELD OF THE INVENTION

The present invention relates generally to implantable medical devices, and more particularly to a low resistivity, high strength, fatigue resistant electrode that may be incorporated in an implantable transvenous cardioverting/defibrillating cardiac lead.

BACKGROUND

Various kinds of implantable medical leads for providing stimulation to selected body tissue have become available. For example, an implantable cardiac lead delivers electrical therapy to a patient's heart through one or more electrodes on the distal end of the lead. The electrodes are connected via electrical conductors to a connector assembly on the proximal end of the lead. The connector assembly is in turn coupled to an implantable medical device (IMD) such as a pacemaker or an implantable cardioverter/defibrillator (ICD) or to an IMD combining both pacemaker and ICD functions.

Presently available transvenous defibrillation leads typically employ shocking electrodes composed of helically wound coils. These electrodes may include at least one coil that may be made of single or multifilar wire, or of multiple, braided coils each of which may be made of single or multifilar wire.

It is important that the electrical resistance of the defibrillating electrode be minimized so as to minimize $I^2R$ losses and maximize the energy delivered to the surrounding tissue so as to preserve battery life. Losses of energy within the coil material are manifested by heat generated in the shocking coil that reduces the efficacy of the cardioverting and/or defibrillating shock. Typical helical coil shocking electrodes are made of solid platinum/iridium alloy wire or platinum clad MP35N alloy. Although having satisfactory corrosion and fatigue resistance, these materials have relatively high electrical resistances, for example, about 3 and about 7 ohms/ft., respectively. Electrode coils made of drawn filled tube (DFT) or drawn brazed strand (DBS) MP35N filled with silver have satisfactory electrical properties but are potentially toxic due to the silver and exhibit low fatigue life.

In addition to electrical considerations, a shocking electrode must have sufficient mechanical strength and fatigue resistance to withstand the repetitive motion of the beating heart over the device's life typically measured in years. Furthermore, the electrode material must resist corrosion and be chemically inactive so as to preclude toxic reactions. Materials such as silver, copper and nickel can be toxic and are susceptible to corrosion.

Accordingly, a shocking electrode should comprise a carefully selected combination of electrical, mechanical and chemical attributes for optimum shocking efficiency and long life.

SUMMARY

In accordance with one, specific, exemplary embodiment, there is provided an implantable medical device electrode comprising at least one biocompatible, biostable, corrosion-resistant wire strand comprising a core comprising a plurality of electrically conductive, low electrical resistance filaments embedded in an electrically conductive matrix, and a low electrical resistance, substantially chemically inactive cladding.

In accordance with yet another specific, exemplary embodiment, there is provided an implantable cardiac lead for transmitting electrical signals between an implantable medical device and selected body tissue in the heart, the lead comprising a lead body having a proximal end and a distal end, the proximal end of the lead body carrying a connector assembly connectable to the implantable medical device, and at least one electrode on the distal end of the lead body, the at least one electrode being electrically connected to a terminal contact on the connector assembly, the at least one electrode comprising a biocompatible, biostable, corrosion-resistant wire strand comprising (a) a core comprising a plurality of electrically conductive, low electrical resistance filaments embedded in an electrically conductive matrix and (b) a low electrical resistance, substantially chemically inactive cladding enclosing the core.

BRIEF DESCRIPTION OF THE DRAWINGS

The foregoing and other objects, features and advantages will be evident to those skilled in the art from the detailed description below, taken together with the accompanying drawings, in which:

FIG. 1 is a side view of an implantable cardiac pacing, sensing and cardioverting/defibrillating system, including a lead carrying a cardioverting/defibrillating electrode accordance with one specific, exemplary embodiment;

FIG. 2 is a side view of the distal portion of an implantable cardiac pacing, sensing and cardioverting/defibrillating lead carrying a pair of spaced-apart cardioverting/defibrillating electrodes in accordance with an alternative embodiment;

FIG. 3 is an enlarged axial cross section view of a portion of the lead in FIG. 1 showing details of the structure of the cardioverting/defibrillating electrode.

DETAILED DESCRIPTION

Figure 4:
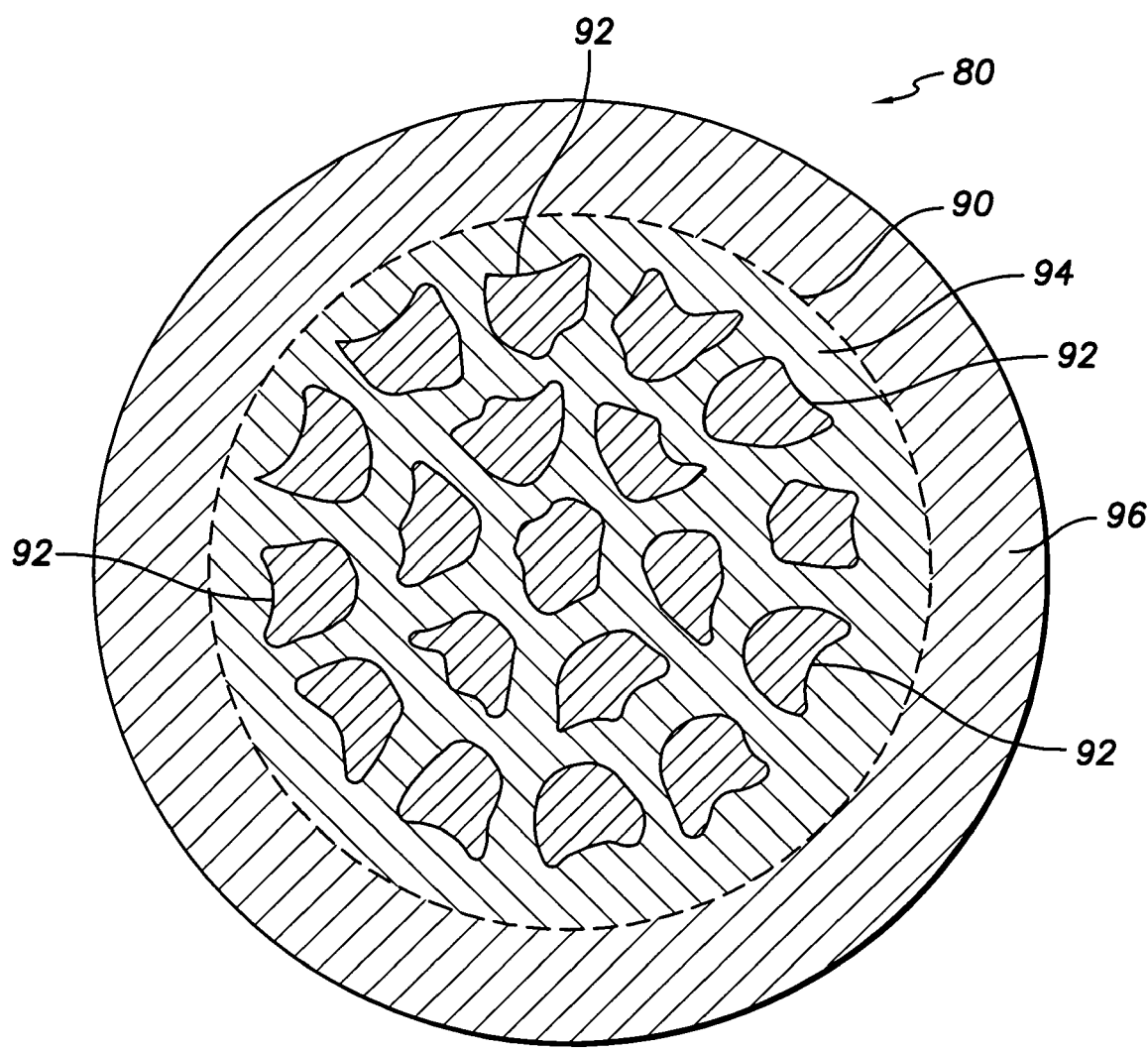
FIG. 4 is an enlarged, transverse cross section view of a wire strand forming part of the lead.

The following description is of a best mode presently contemplated for making the cardioverting/defibrillating electrode. This description is not to be taken in a limiting sense but is made merely for the purpose of describing the general principles of the cardioverting/defibrillating electrode. Although the invention will be described in the context of implantable cardiac stimulation and sensing leads, it will be evident to those skilled in the art that the cardioverting/defibrillating electrode described herein has broader utility, being applicable to a wide variety of implantable medical leads for stimulating selected body tissue and sensing the electrical activity of such tissue. Further, although the cardioverting/defibrillating electrode is described herein in the context of a shocking electrode, it will be evident that it is applicable to a wide range of electrodes, including, without limitation, pacing and/or sensing electrodes, whether wound around a lead body or otherwise configured.

By way of example and not limitation, FIG. 1 shows an endocardial pacing, sensing and defibrillating system 10 comprising a lead 12 and an implantable medical device (IMD) 14 that may comprise a pacemaker/ICD. The lead 12 includes a lead body 16 having a proximal end 18 and a distal end 20. The proximal end 18 of the lead 12 incorporates a connector assembly 22 compatible with a standard such as the IS-4 standard for connecting the lead body to the IMD 14. In the example shown in FIG. 1, the connector assembly 22 includes a tubular pin terminal contact 24 and two ring terminal contacts 26 and 28 electrically coupled to electrodes along the distal end 20 of the lead body. The connector assembly 22 of the lead is received within a receptacle (not shown) in the IMD 14 containing electrical terminals positioned to engage the contacts 24, 26 and 28 on the connector assembly 22. As is well known in the art, to prevent ingress of body fluids into the receptacle, the connector assembly 22 is provided with spaced sets of seals 30. In accordance with standard implantation techniques, a stylet or guide wire (not shown) for delivering and steering the distal end of the lead body during implantation is inserted into a lumen of the lead body through the tubular connector terminal pin 24.

The lead body 16 extends along a central, longitudinal axis 32 and preferably comprises a tubular sheath or housing 34 made of an insulating, biocompatible, biostable polymer, for example, silicone rubber or polyurethane and having an outer surface 36. Although various insulating housing materials may be used, silicone rubber is often preferred because of its flexibility and long term biostability.

The distal end 20 of the lead body may carry one or more electrodes whose configurations, functions and placement along the length of the distal end will be dictated by the indicated stimulation therapy, the peculiarities of the patient's anatomy, and so forth. The lead body 16 illustrates but one example of the various combinations of stimulating and/or sensing electrodes that may be utilized. In accordance with one illustrative embodiment, at least one of the electrodes comprises a cardioverting and/or defibrillating electrode 40 electrically connected by means of an electrical conductor 42 to one of the contacts 24, 26 or 28 on the connector assembly 22. The distal end of the lead body 16 also carries a tip electrode 44 and a ring electrode 46 coupled to corresponding ones of the contacts 24, 26 and 28 on the connector assembly 22 by means of electrical conductors collectively identified by the reference numeral 48.

In conventional fashion, the distal end 20 of the lead body may include passive fixation means that may take the form of projecting tines 50 for anchoring the lead body within a chamber of the heart. Alternatively or in addition thereto, the passive fixation or anchoring means may comprise one or more preformed humps, spirals, S-shaped bends, or other configurations manufactured into the distal end 20 of the lead body 16 where the lead is intended for left heart placement within a vessel of the coronary sinus region. The fixation means may also comprise an active fixation mechanism such as a helix. It will be evident to those skilled in the art that any combination of the foregoing fixation or anchoring means may be employed.

As shown in FIG. 2, the distal end of the lead body may carry more than one ring electrode as well as more than one cardioverting/defibrillating coil. In the example of FIG. 2, there is shown a portion of a lead body 60 having a distal end 62 carrying a tip electrode 64, two ring electrodes 66 and 68 and two spaced-apart cardioverting/defibrillating coils 70 and 72 wound about an outer surface 74 of the lead body. The electrodes are coupled to contacts on a connector assembly (not shown in FIG. 2) on the proximal end of the lead body 60 by means of conductors identified collectively by the reference numeral 76. Other electrode configurations may, of course, be employed pursuant to lead constructions well known in the art. For example, an alternative electrode arrangement may include additional ring stimulation and/or sensing electrodes as well as additional cardioverting and/or defibrillating coils spaced apart along the distal end of the lead body. Thus, as emphasized, FIGS. 1 and 2 are illustrative only; the distal end of the lead body may, for example, carry only cardioverting/defibrillating electrodes or a combination of pacing, sensing and cardioverting/defibrillating electrodes. The defibrillating electrodes are preferably of coil design and for greater lead flexibility may comprise spaced apart, relatively short coils.

The lead bodies 16 and 60 may be isodiametric, that is, the outside diameter of the lead body may be the same throughout its entire length. By way of example and not limitation, the outside diameter of the lead bodies may range from about 0.026 inch (2 F) to about 0.130 inch (10 F). Also, in accordance with well known techniques, the outer surface of the lead bodies may have a lubricious coating along their lengths to facilitate their movement through a lead delivery introducer and the patient's vascular system. Further, the electrical conductors 42, 48 and 76 may be in the form of multifilar, braided cables typically of MP35N or MP35N/Ag alloy, or monofilament, non-coiled wires of, for example, nitinol, MP35N, or the like, all well known in the art. Alternatively, one or more of the conductors may be formed of coiled flat or ribbon wire.

Taking the cardioverting/defibrillating electrode 40 as representative and with reference also to FIG. 3, the electrode 40 is in the form of a coil comprising a wire strand 80 wound about the outer surface 36 of the distal end 20 of the lead body 16. Preferably, the wire strand 80 is closely wound with adjacent turns thereof in mechanical and electrical contact along their helical length. Alternatively, the adjacent turns of the coiled strand may be spaced apart; FIG. 3 shows an embodiment combining both. In FIG. 3, the coil electrode 40 includes spaced apart turns 82 and several closely wound turns 84 in contact along a helical contact region 86. Further, as is well-known in the art, the turns may be arranged as interleaved, multifilar windings with the various windings electrically connected in parallel for redundancy.

In accordance with one illustrative embodiment, the wire strand 80 comprises a composite, biocompatible, biostable structure characterized by high strength, fatigue and corrosion resistance, chemical inertness, and low electrical resistance.

More specifically, and with reference now also to FIG. 4, the wire strand 80 includes a core 90 comprising a plurality of electrically conductive, low electrical resistance filaments 92 embedded in a high strength, electrically conductive matrix 94. A cladding layer 96 comprising a low electrical resistance, substantially chemically inactive material covers the core 90. Preferably, the core 90 comprises a drawn filled tubing (DFT) structure providing a tightly clustered structure substantially devoid of interstices or voids that would otherwise promote crevice corrosion. Alternatively, the core 90 may comprise a drawn brazed strand (DBS). Both DFT and DBS processes are well known in the art.

The core 90 preferably comprises a 1×N structure where N may be 2 or more. In accordance with one practical embodiment, the core comprises a 1×19 array, that is, a single core strand containing nineteen filaments 92.

Each of the plurality of core filaments 92 comprises a low electrical resistance material such as silver, gold or a low electrically resistant conductive polymer; silver is preferred. The drawing fabrication process uniformly spreads the matrix 94 to fill voids about the filaments 92 that, if made of a material such as silver, could potentially be the source of corrosion and/or toxic reactions with the surrounding body tissue. As is known, conductive polymers fall into two general categories: intrinsically conductive and conductor-filled. Intrinsically conductive polymers include polyacetylene, polypyrrole, and polyaniline, among others. Alternatively, conductor-filled polymers may include presently available materials approved for implantation such as silicone rubber having embedded therein metallic, carbon or graphite particles or powder. Silver-filled silicone rubbers of the kind manufactured by NuSil or Specialty Silicone Products, modified so as to be approved for implantation, are of potential utility. An example is silver-coated, nickel-filled silicone rubber sold as NuSil R2637.

The matrix 94 comprises a material such as MP35N, tantalum, titanium, niobium, or other suitable metal, MP35N being preferred. Although MP35N has a relatively high electrical resistance compared to, for example, silver and relatively poor corrosion resistance, it is relatively inexpensive, has high mechanical strength and flows well around the filaments 92 when the material is drawn thereby providing the desired void-free final core structure. Although platinum may be used for this purpose, its expense may make it prohibitive commercially. Tantalum, with an electrical resistance lower than MP35N, is also a feasible matrix material. The main object is to provide a core comprising low electrical resistance, high strength, fatigue resistant filaments firmly and tightly embedded within a drawable, electrically conductive high strength material. A preferred, commercially practical core comprises a 1×19 strand containing silver filaments embedded in a matrix of MP35N alloy. Further, a preferred core composition may comprise 10-35% by weight of filaments with the remainder comprising MP35N. In addition, the filaments may be braided for enhanced fatigue resistance.

The cladding 96, which is preferably highly corrosion resistant, substantially chemically inert or inactive, and of low electrical resistance, may be made of platinum, iridium, rhodium, palladium, or alloys of the foregoing including but not limited to platinum/iridium 90/10 or 80/20 alloy; platinum is the preferred material.

Where the adjacent turns of the coiled wire strand 80 are spaced apart, electrical current is constrained to follow a helical path. By closely winding the strand 80 so that adjacent turns (such as the turns 84 in FIG. 3) are in physical contact so as to establish electrical communication therebetween, it will be seen that electrical current represented by the arrows 100 can also flow axially through the contacting regions 86 of the cladding 96 of the adjacent turns. The overall electrical resistance of the helical coil electrode 40 is thereby further reduced so as to increase the electrical efficiency and shocking efficacy of the coil thereby adding to the longevity of the implantable medical device battery and reducing the voltage or energy required for defibrillation. The decrease in delivered energy can result in a corresponding decrease in patient trauma and in demand on the device's power source.

Platinum clad drawn DFT in accordance with one illustrative embodiment, comprising a 1×19 wire strand core including silver filaments in a matrix of MP35N alloy, exhibits a resistance of 0.9 ohms per foot, substantially lower than typical, conventional shocking coil materials.

A wire strand in accordance with one illustrative embodiment may be fabricated by first assembling an MP35N tube filled with a silver filament core. This assembly is then drawn in stages providing a drawn filled tubing structure in accordance with techniques well known in the art. DFT has an overall circular cross section; the silver filaments also retain their circular cross sections. This composite material, however, has interstitial spaces that, without further processing, may be subject to corrosion. Accordingly, pursuant to another illustrative embodiment, platinum is placed about the DFT and this cladded platinum DFT assembly is drawn again, preferably in several alternating cold-working and annealing stages. This second drawing process subjects the core 90 to radial compression so that the matrix 94 squeezes down on the silver filaments during the drawing process, causing the elimination of substantially all of the interstices and forming a pressure weld along the interface of the core and cladding. At the same time, as shown in FIG. 4, the cross sections of the highly stressed silver filaments change from circular to irregular shapes. The platinum may be applied to the DFT exterior in any known fashion prior to its being drawn, for example, as an outer tube. Alternatively, the platinum may be deposited in various known ways, for example, by sputtering although such techniques may be less desirable.

While several illustrative embodiments have been shown and described, numerous variations and alternative embodiments will occur to those skilled in the art. Such variations and alternative embodiments are contemplated, and can be made without departing from the spirit and scope of the invention as defined in the appended claims.

What is claimed is:

1. An implantable cardiac lead for transmitting electrical signals between an implantable medical device and selected body tissue in the heart, the lead comprising:

a lead body having a proximal end and a distal end, the proximal end of the lead body carrying a connector assembly connectable to the implantable medical device; and at least one cardioverting and/or defibrillating coil electrode on the distal end of the lead body, the at least one cardioverting and/or defibrillating coil electrode being electrically connected to a terminal contact on the connector assembly, the at least one cardioverting and/or defibrillating coil electrode comprising a biocompatible, biostable, corrosion-resistant wire strand comprising (a) a core comprising a plurality of electrically conductive, low electrical resistance filaments embedded in an electrically conductive matrix and (b) a low electrical resistance, substantially chemically inactive cladding enclosing the core, the cladding being discrete from the matrix.

2. The lead of claim 1 further comprising:
at least one pacing and/or sensing electrode.

3. The lead of claim 1 in which:
the core of the wire strand is substantially devoid of interstices.

4. The lead of claim 1 in which:
the filaments are braided.

* * * * *